United States Patent [19]
Hellendahl et al.

[11] Patent Number: 6,090,807
[45] Date of Patent: *Jul. 18, 2000

[54] USE OF HETEROCYCLIC COMPOUNDS

[75] Inventors: Beate Hellendahl, Schifferstadt; Annegret Lansky, Darmstadt; Beatrice Rendenbach-Müller, Neustadt; Alfred Bach, Heidelberg; Liliane Unger, Ludwigshafen; Hans-Jürgen Teschendorf, Dudenhofen; Carsten Wicke, Altrip, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,181
[22] PCT Filed: Jul. 14, 1995
[86] PCT No.: PCT/EP95/02782
  § 371 Date: Jan. 14, 1997
  § 102(e) Date: Jan. 14, 1997
[87] PCT Pub. No.: WO96/02246
  PCT Pub. Date: Feb. 1, 1996

[30] Foreign Application Priority Data

Jul. 15, 1994 [DE] Germany ............... 44 25 146

[51] Int. Cl.⁷ ................ A61K 31/495; A61K 31/455; A61K 31/44
[52] U.S. Cl. ................ 514/252; 514/326; 514/335; 514/332; 514/358; 514/354; 514/355; 514/356; 514/357
[58] Field of Search ............ 424/250; 514/252, 514/326, 332, 335, 352, 354, 355, 356, 357

[56] References Cited

U.S. PATENT DOCUMENTS

| | | | |
|---|---|---|---|
| 3,362,956 | 1/1968 | Archer | 260/268 |
| 3,491,097 | 1/1970 | Koppe | 260/268 |
| 3,821,234 | 6/1974 | Koppe | 260/295 |
| 3,839,336 | 10/1974 | Borck | 260/268 |
| 4,021,555 | 5/1977 | Seyfried et al. | 424/250 |
| 4,123,529 | 10/1978 | Verge | 424/250 |
| 4,404,382 | 9/1983 | Gall | 544/360 |
| 5,254,552 | 10/1993 | Abou-Gharbia | 514/252 |
| 5,395,835 | 3/1995 | Glase | 514/254 |
| 5,403,842 | 4/1995 | Leonardi | 514/252 |
| 5,498,628 | 3/1996 | Rognan et al. | |

FOREIGN PATENT DOCUMENTS

| | | |
|---|---|---|
| 512 755 | 11/1992 | European Pat. Off. . |
| 2213808 | 3/1972 | Germany . |
| 2258033 | 11/1972 | Germany . |

OTHER PUBLICATIONS

Marpat Abstract, AN 117: 233859, Fukazawa et al, Corresponding to Japanese patent JP 04134070 AZ, May 7, 1992.

Murray et al., *Bio. & Med. Chem. Lett.*, vol. 5, No. 3, pp. 219–222, 1995.

U.S. application No. 07/765,292, Hellendahl et al., filed Nov. 14, 1997.

U.S. application No. 08/765,915, Hellendahl et al., filed Nov. 14, 1997.

U.S. application No. 08/765,916.

*Primary Examiner*—Keith D. MacMillan
*Attorney, Agent, or Firm*—Keil & Weinkauf

[57] ABSTRACT

The present invention relate to the use of heterocyclic compounds of the following formula:

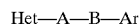

where Het, A, B and Ar have the meanings stated in the description. The compounds according to the invention have a high affinity for the dopamine $D_3$ receptor and can therefore be used to treat disorders which respond to dopamine $D_3$ ligands.

10 Claims, No Drawings

USE OF HETEROCYCLIC COMPOUNDS

This application is a 371 of PCT/EP95/02782, filed Jul. 14, 1995, which claims priority of Fed. Ref. Germany Application P 44 25 146.7, filed Jul. 14, 1994.

The invention relates to the use of heterocyclic compounds. Said compounds have valuable therapeutic properties and can be used to treat disorders which respond to dopamine $D_3$ receptor ligands.

Compounds of the type under discussion here and having physiological activity have been disclosed. Thus, U.S. Pat. No. 4,404,382 describes corresponding imidazole compounds with antiallergic activity.

U.S. Pat. No. 3,362,956 likewise describes imidazole compounds of this type. The latter have adrenolytic and anticonvulsant activity.

DE-A-22 58 033 describes pyrazole compounds with central depressant activity.

DE-A-27 17 415 describes furan, thiophene, oxazole and thiadiazole compounds which can be used to treat hypersensitivity disorders.

Neurous obtain their information inter alia via G protein-coupled receptors. There are numerous substances which exert their effect via these receptors. One of them is dopamine.

There is confirmed evidence of the presence of dopamine and its physiological function as neurotransmitter. Cells which respond to dopamine are involved in the etiology of schizophrenia and Parkinson's disease. These and other disorders are treated with drugs which interact with dopamine receptors.

By 1990, two subtypes of dopamine receptors had been clearly defined pharmacologically, namely $D_1$ and $D_2$ receptors.

Sokoloff et al., Nature 1990, 347: 164-151, found a third subtype, namely $D_3$ receptors. They are expressed mainly in the limbic system. The $D_3$ receptors differ structurally from the $D_1$ and $D_2$ receptors in about half the amino acid residues.

The effect of neuroleptics has generally been ascribed to their affinity for $D_2$ receptors. Recent receptor-binding studies have confirmed this. These showed that most dopamine antagonists, such as neuroleptics, have high affinity for $D_2$ receptors but only low affinity for $D_3$ receptors.

The prior art compounds described above are such $D_2$ receptor agonists and antagonists.

It has now been found, surprisingly, that the compounds according to the invention have a high affinity for the dopamine $D_3$ receptor and only a low affinity for the $D_2$ receptor. They are thus selective $D_3$ ligands.

The present invention therefore relates to the use of compounds of the formula I:

Het—A—B—Ar where

A is a straight-chain or branched $C_1$–$C_{18}$-alkylene group which may comprise at least one group which is selected from among O, S, $NR^4$, $CONR^4$, $NR^4CO$, COO, OCO and a double or triple bond, B is a radical of the formula:

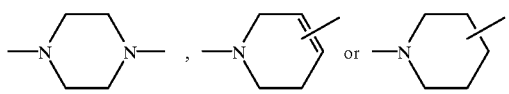

Ar is phenyl, pyridyl, pyrimidyl or triazinyl, where Ar may have one to four substituents which are, independently of one another, selected from among $OR^4$, $C_1$–$C_8$-alkyl, $C_2$–$C_8$-alkenyl, $C_2$–$C_8$-alkynyl, halogen, CN, $CO_2R^4$, $NO_2$, $SO_2R^4$, $SO_3R^4$, $NR^4R^5$, $SO_2NR^5R^5$, $SR^4$, $CF_3$, $CHF_2$, a 5- or 6-membered carbocyclic, aromatic or non-aromatic ring and a 5- or 6-membered heterocyclic, aromatic or non-aromatic ring having 1 to 3 hetero atoms which are selected from among O, S and N, where the carbocyclic or the heterocyclic ring is unsubstituted or substituted by $C_1$–$C_8$-alkyl, halogen, $OC_1$-$C_8$-alkyl, OH, $NO_2$ or $CF_3$, and where Ar may also be fused to a carbocyclic or heterocyclic ring of the type defined above, Het is a group which is selected from among

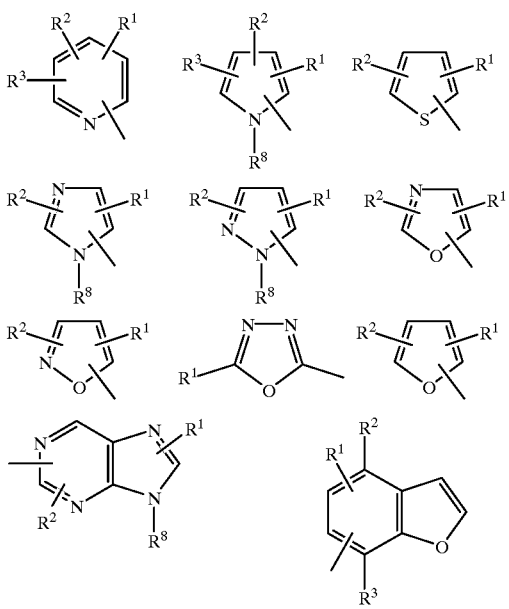

where
$R^1$, $R^2$ and $R^3$ are, independently of one another, H, halogen, $OR^5$, $NR^4R^5_1$, $SR^4$, $CF_3$, CN, $CO_2R^4$ or $C_1$–$C_8$-alkyl which is unsubstituted or substituted by OH, $OC_1$-$C_8$-alkyl or halogen, $R^4$ is H or $C_1$–$C_8$-alkyl which is unsubstituted or substituted by OH, $OC_1$-$C_3$-alkyl or halogen;

$R^5$ has the meanings indicated for $R^4$ or is $COR^4$ or $CO_2R^4$;

$R^8$ has the meanings indicated for $R^5$, and the salts thereof with physiologically tolerated acids, for the production of a pharmaceutical composition for treating disorders which respond to dopamine $D_3$ receptor antagonists or agonists.

The compounds according to the invention are selective dopamine $D_3$ receptor ligands which intervene regioselectively in the limbic system. Because of their low affinity for the $D_2$ receptor, they have fewer side effects than the classical neuroleptics which are $D_2$ antagonists. The compounds can therefore be used to treat disorders which respond to dopamine $D_3$ receptor antagonists or agonists, eg. to treat disorders of the central nervous system, in particular schizophrenia, depression, neuroses and psychoses. They can additionally be used to treat sleep disturbances and nausea and as antihistamines.

For the purpose of the present invention, the following terms have the meanings indicated below:

Alkyl (also in radicals such as alkoxy, alkylamino etc.) means a straight-chain or branched alkyl group having 1 to 8 carbon atoms, preferably 1 to 6 carbon atoms and, in particular, 1 to 4 carbon atoms. The alkyl group may have one or more substituents which are selected, independently of one another, from among OH and $OC_1$-$C_8$-alkyl.

Examples of an alkyl group are methyl, ethyl, n-propyl, i-propyl, n-butyl, isobutyl, t-butyl, etc.

Alkylene stands for straight-chain or branched radicals with, preferably, 2 to 10 carbon atoms, particularly preferably 3 to 8 carbon atoms and, in particular, 3 to 6 carbon atoms.

The alkylene groups may comprise at least one of the abovementioned groups. This can—just like the double or triple bond mentioned—be arranged in the alkylene chain at any point or at the end of the chain so that it connects the chain to the heterocyclic radical. The latter is preferred. When the alkylene group comprises a double or triple bond, it has at least three carbon atoms in the chain.

Halogen is F, Cl, Br, I and, in particular, Cl, Br, I.

The radical Ar may have one, two, three or four substituents. The substituents may be located at any position on the phenyl ring. Preferably, however, at least one is in the m position.

Preferably, they are, independently of one another, selected from among H, $C_1$-$C_8$-alkyl, $OC_1$-$C_8$-alkyl, $CHF_2$, $CF_3$, CN, halogen, $SO_2OR^4$ and $CO_2R^4$.

Ar preferably has at least one substituent and is, in particular,

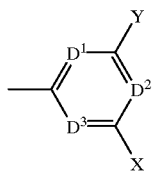

where $D^1$, $D^2$ and $D^3$ are, independently of one another, CH or N, and X and Y are H or have the meanings indicated above or below.

$D^1$, $D^2$ and $D^3$ are preferably CH or $D^1$ is N and $D^2$ and $D^3$ are CH. When one of the substituents of the radical Ar is a 5- or 6-membered heterocyclic ring, examples thereof are a pyrrolidine, piperidine, morpholine, piperazine, pyridine, pyrimidine, triazine, pyrrole, thiophene, thiazole, imidazole, oxazole, isoxazole, pyrazole or thiadiazole residue.

When one of the substituents of the radical Ar is a carbocyclic radical, it is, in particular, a phenyl, cyclophenyl or cyclohexyl radical.

When one of the substituents of the radical Ar is $C_1$-$C_8$-alkyl, a branched radical, in particular the isopropyl or t-butyl group, is preferred.

When Ar is fused to a carbocyclic or heterocyclic radical, Ar is, in particular, a naphthalene, di- or tetrahydronaphthalene, quinoline, di- or tetrahydroquinoline, indole, dihydroindole, benzimidazole, benzothiazole, benzothiadiazole, benzopyrrole or benzotriazole residue.

A preferred embodiment comprises the compounds of the formula I where A is $C_1$-$C_8$-alkylene which may comprise an oxygen or sulfur atom or the group $CONR^4$, in particular O or S.

Another preferred embodiment comprises the compounds of the formula I where Het is a group of the following general formulae:

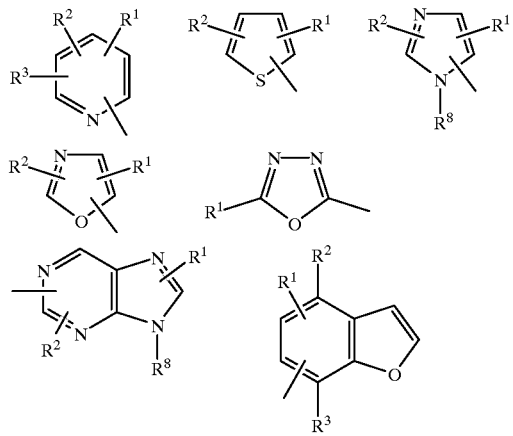

Another preferred embodiment comprises the compounds of the formula I where Bet is a group of the following general formulae:

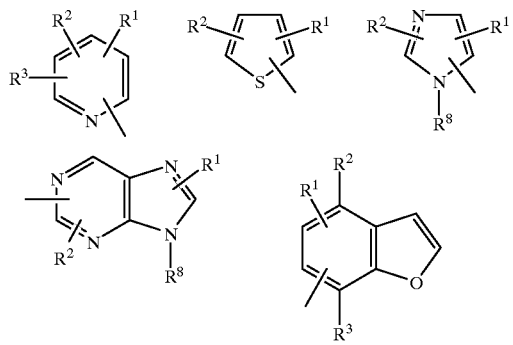

Another preferred embodiment comprises the compounds of the formula I where Het is a group of the general formulae:

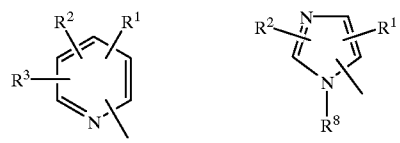

In these, $R^1$, $R^2$, $R^3$ and $R^8$ always have the meanings indicated above.

$R^1$, $R^2$ and $R^3$ are preferably, independently of one another, H, $NR^4R^5$, $OR^5$, $C_1$-$C_8$-alkyl, $CO_2R^4$, $CF_3$ or halogen.

The Het radical preferably has one or two, in particular one, substituent.

When Het is a pyridine residue, $R^1$, $R^2$ and $R^3$ are preferably selected, independently, from among H, halogen, $OR^5$, $NR^4R^5$, $CF_3$, $CO_2R^4$ and $C_1$-$C_8$-alkyl.

When Het is a thiophene residue, $R^1$ and $R^2$ are preferably selected, independently, from among halogen and $C_1$-$C_8$-alkyl.

When Het is a purine residue, A is preferably S—$C_4$-$C_7$-alkyl.

In another embodiment, A is a $C_3$-$C_6$-alkylene group which may comprise S, O or $CONR^4$.

X is preferably H, $CF_3$, CN, halogen, $NO_2$, $CHF_2$, $C_1$–$C_8$-alkyl, in particular $C_2$–$C_4$-alkyl, $SO_2R^4$ or $CO_2R^4$ and in particular H, $CF_3$, halogen, $CHF_2$, $C_1$–$C_8$-alkyl or CN. X is particularly preferably $CF_3$. $CHF_2$ or $C_2$–$C_4$-alkyl.

Y is preferably $C_1$–$C_8$-alkyl, in particular $C_2$–$C_4$-alkyl, or hydrogen.

A particularly preferred embodiment comprises the compounds of the formula I$a$:

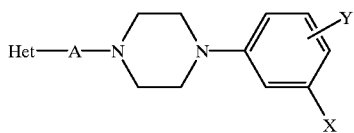

and, in particular, the compounds of the formula I$b$:

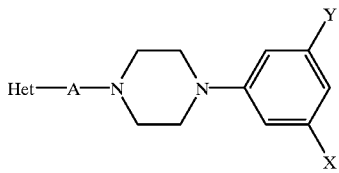

where A, Het, X and Y have the meanings indicated above. In the formulae I$a$ and I$b$ in particular X is $CF_3$ and Y is H or X and Y are both $C_1$–$C_8$-alkyl.

The invention also embraces the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung, volume 10, pages 224 et seq., Birkhäuser Verlag, Basle and Stuttgart, 1966.

The compounds of the formula I may have one or more centers of asymmetry. The invention therefore includes not only the racemates but also the relevant enantiomers and diastereomers. The invention also includes the tautomeric forms in each case.

Those compounds of the formula I which are novel are prepared in a similar manner to the prior art mentioned at the outset, using methods familiar to the skilled worker.

To treat the abovementioned disorders, the compounds according to the invention are administered in a conventional manner orally or parenterally (subcutaneously, intravenously, intramuscularly, intraperitoneally). Administration can also take place with vapors or sprays through the nasopharyngeal space.

The dosage depends on the age, condition and weight of the patient and on the mode of administration. As a rule, the daily dose of active substance is about 10 to 1000 mg per patient and day on oral administration and about 1 to 500 mg per patient and day on parenteral administration.

The invention also relates to pharmaceutical compositions which contain the compounds according to the invention. These compositions are in the usual solid or liquid pharmaceutical administration forms, for example as tablets, film-coated tablets, capsules, powders, granules, sugar-coated tablets, suppositories, solutions or sprays. The active substances can in these cases be processed with conventional pharmaceutical aids such as tablet binders, fillers, preservatives, plasticizers, wetting agents, dispersants, emulsifiers, solvents, release-slowing agents, antioxidants and/or propellant gases (cf. H. Sucker et al., Pharmazeutische Technologie, Thieme-Verlag, Stuttgart, 1978). The administration forms obtained in this way normally contain the active substance in an amount of from 1 to 99% by weight.

The following examples serve to explain the invention without limiting it.

EXAMPLE 1

2-[3-(4-{3-Trifluoromethylphenyl}piperazinyl)propylthio] pyridine

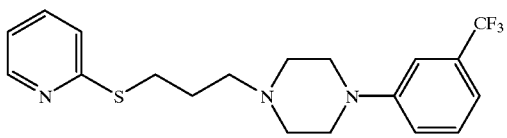

a) 1-(3-Chloropropyl)-4-(3-trifluoromethlphenyl)-piperazine 30 g (0.13 mol) of trifluoromethylphenyl-piperazine, 23 g (0.146 mol) of 1-bromo-3-chloropropane and 15 g (0.148 mol) of triethylamine in 200 ml of THF were refluxed for 4 hours. Cooling was followed by filtration with suction and concentration. The viscous residue was taken up in ethyl acetate, washed with water, dried over $MgSO_4$ and then concentrated. The resulting residue comprised 39 g of product as yellowish oil (quantitative yield).

b) 2-[3-(4-{Trifluoromethylphenyl}piperazinyl) propylthio]pyridine 1.11 g (10 mmol) of 2-mercaptopyridine, 3.1 g (10.1 mmol) of 1-(3-chloropropyl)-4-(3-trifluoromethylphenyl) piperazine and 1.5 g (15 mmol) of triethylamine in 5 ml of DMF were stirred at 100° C. for 1 hour. The mixture was then poured into 5% strength hydrochloric acid and extracted with ethyl acetate. The aqueous phase was made alkaline with sodium hydroxide solution and again extracted with ethyl acetate, and the organic phase was dried over $MgSO_4$ and concentrated. The residue was purified by chromatography (mobile phase: $CH_2Cl_2/CH_3OH$=98/2).

2.5 g of product were obtained as yellowish oil (=65% yield).

H-NMR [δ, ppm]: 1.95 (2H); 2.55 (2H); 2.62 (4H); 3.23 (6H); 6.95 (1H); 7.05 (3H); 7.17 (1H); 7.36 (1H); 7.48 (1H); 8.42 (1H)

EXAMPLE 2

2-[5-(4-{3-Trifluoromethylphenyl}piperazinyl) pentylmercapto] pyridine

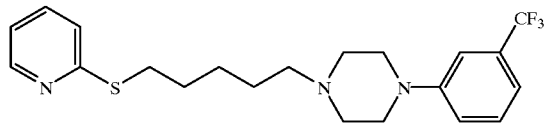

a) 2-(5-Chloropentylmercapto)pyridine 2.78 g (25 mmol) of 2-mercaptopyridine, 4.64 g (25 mmol) of 1-bromo-5-chloropentane and 2.58 g (25.5 mmol) of triethylamine in 100 ml of THF were refluxed for 4 hours. Cooling was followed by filtration with suction, concentration and purification of the residue by chromatography (mobile phase: cyclohexane/ethyl acetate=92/8). 4 g of product were obtained (=74% yield).

b) 2-[5-(4-{3-Trifluoromethylphenyl}piperazinyl) pentylmercapto]pyridine 2.37 g (11 mmol) of 2-(5-chloropentyl-mercapto) pyridine, 2.78 g (12 mmol) of m-trifluoromethylphenylpiperazine and 1.22 g (12.1 mmol) of triethylamine in 5 ml of DMF were stirred at 90° C. for 5 hours. The mixture was then poured into water and extracted three times with $CH_2Cl_2$, followed by drying over $MgSO_4$ and concentrating. The residue was mixed with methyl t-butyl ether and filtered off with suction, and the mother liquor was concentrated. Purification by chromatography (mobile phase: $CH_2Cl_2/CH_3OH=96/4$) resulted in 3.0 g of product as oil (=67% yield).

H=NMR [δ; ppm]: 1.5 (4H); 1.75 (2H); 2.4 (2H); 2.6 (4H); 3.2 (2H); 3.25 (4H); 7.0 (1H); 7.1 (3H); 7.2 (1H); 7.35 (1H); 7.45 (1H); 8.4 (1H)

EXAMPLE 3

3-[3-(4-{3-Trifluoromethylphenyl}piperazinyl)propylamino-carbonyl]thiophene

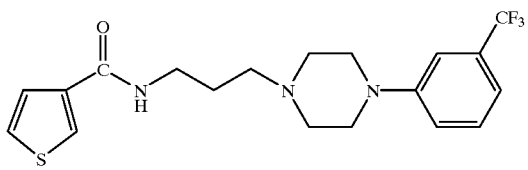

A mixture of 0.76 g (5.9 mmol) of 3-thiophene-carboxylic acid, 1.0 g (6.2 mmol) of carbonyldiiizidazole and 1 spatula tip of dimethylaminopyridine in $CH_2Cl_2$ was stirred at room temperature for ½ h. 1.9 g (5.9 mmol) of N-(3-trifluoromethylphenyl)-N'-(3-aminopropyl)piperazine were added dropwise to this mixture, which was further stirred at room temperature overnight. Aqueous workup was followed by chromatography on $SiO_2$ (mobile phase: $CH_{2Cl2}/CH_3OH=10:1$). The resulting oil was dissolved in a little $CH_3OH$. Addition of 0.64 g (5.5 mmol) of fumaric acid in $CH_2Cl_2$ resulted in 1.3 g of product as white solid. Melting point: 124–125° C.

EXAMPLE 4

2-[2-(4-{3-Trifluoromethylphenyl}piperazinyl)ethylaminocarbonyl]pyridine

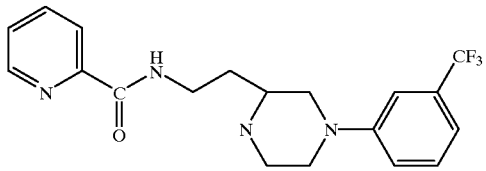

0.74 ml of chloroethyl formate was added dropwise to a solution of 0.95 g of 2-pyridinecarboxylic acid and 1.1 ml of $NEt_3$ in $CH_2Cl_2$ at 0° C. After stirring at room temperature for 15 min, the mixture was again cooled and 2 g of N-(3-trifluoromethylphenyl)-N'-(2-aminoethyl)-piperazine were added dropwise. The mixture was then stirred at room temperature for 3 h, washed with $H_2O$, $NH_4Cl$ solution, NaOH and $H_2O$, dried over $MgSO_4$ and concentrated. Recrystallization from ethyl acetate/heptane resulted in 1.9 g of product. Melting point: 108–110° C.

EXAMPLE 5

2-[3-(4-{3-Trifluoromethylphenyl}piperazinyl)propylamino-carbonylmethyl]pyridine

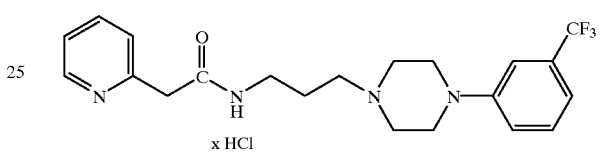

x HCl 2.87 g of N-(3-trifluoromethylphenyl)-N'-(3-aminopropyl)-piperazine were added dropwise to a solution of 2.34 g of 2-pyridineacetic acid N-hydroxysuccinimide ester in $CH_2Cl_2$ while cooling. The mixture was stirred at room temperature overnight and subsequently washed with $NaHCO_3$ solution and water. The organic phase was separated off and dried with $MgSO_4$, and the solvent was distilled off. A little $CH_3OH$ was added to the residue, and then ethereal HCl was added dropwise. 2.0 g of product were obtained as white solid. Melting point: 178–179° C.

The following compounds were synthesized in a similar manner:

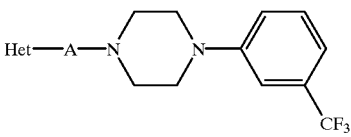

| Example No. | Het | A | Physical data<br>H-NMR [δ, ppm],-<br>Melting Point |
|---|---|---|---|
| 6 | ![purine] | $SCH_2CH_2CH_2$ | 2.07(2H);2.63(6H);3.22(4H);<br>3.45(2H);7.08(3H);7.33(1H);<br>8.22(1H);8.75(1H) |

-continued

| Example No. | Het | A | Physical data H-NMR [δ, ppm].- Melting Point |
|---|---|---|---|
| 7 | EtO₂C-, H₃C- substituted imidazole (2,4-disubstituted-1-methylimidazole) | SCH₂CH₂CH₂ | 1.35(3H);1.92(2H);2.48(3H); 2.65(6H);3.15(2H);3.28(4H); 4.3(2H);7.08(3H);7.35(1H) |
| 8 | 1,2-dimethylimidazole | SCH₂CH₂CH₂ | 1.88(2H);2.5(2H);2.55(4H); 3.1(2H);3.2(4H);3.62(3H); 6.93(1H);7.1(4H);7.35(1H) |
| 9 | 2-methylimidazole | SCH₂CH₂CH₂ | 1.95(2H);2.65(6H);3.08(2H); 3.3(4H);7.05(5H);7.36(1H) |
| 10 | 4-methylpyridine | SCH₂CH₂CH₂ | 1.92(2H);2.5(2H);2.6(4H); 3.08(2H);3.24(4H);7.08(SH); 7.36(1H);8.4(2H) |
| 11 | 2-chloro-6-methylpyridine | OCH₂CH₂CH₂ | 2.0(2H);2.55(2H);2.62(4H); 3.26(4H);4.35(2H);6.63(1H); 6.9(1H);7.1(3H);7.35(1H); 7.53(1H) |
| 12 | 3-hydroxy-2-methylpyridine | OCH₂CH₂CH₂ | 2.1(2H);2.6(6H);3.23(4H); 4.08(2H);6.22(1H);6.8(1H); 7.05(4H);7.32(1H) |
| 13 | 2,6-dimethylpyridine | OCH₂CH₂CH₂ | 2.0(2H);2.45(3H);2.6(2H); 2.65(4H);3.25(4H);4.35(2H); 6.52(1H);6.7(1H);7.08(3H); 7.35(1H);7.45(1H) |
| 14 | 3-hydroxy-2-methylpyridine | SCH₂CH₂CH₂ | 1.9(2H);2.55(2H);2.65(4H); 3.1 (2H);3.3(4H);7.1(5H); 7.35(1H);8.1(1H) |
| 15 | 5-chloro-2-methylpyridine | OCH₂CH₂CH₂ | 2.0(2H);2.55(2H);2.63(4H); 3.25(4H);4.35(2H);6.7(1H); 7.05(3H);7.35(IH);7.52(1H); 8.08(1H) |
| 16 | 2-amino-6-methylpyridine | OCH₂CH₂CH₂ | 2.0(2H);2.6(2H);2.65(4H); 3.25(4H);4.25(4H);6.1(2H); 7.1(3H);7.35(2H) |
| 17 | 5-trifluoromethyl-2-methylpyridine | SCH₂CH₂CH₂ | 1.98(2H);2.58(2H);2.65(4H); 3.3(6H);7.1(3H);7.3(1H); 7.37(1H);7.66(1H);8.66(1H) |

-continued

| Example No. | Het | A | Physical data H-NMR [δ, ppm],- Melting Point |
|---|---|---|---|
| 18 | 3-CO2CH3, 2-methyl pyridine | SCH2CH2CH2 | 2.0(2H);2.55(2H);2.6(4H); 3.23(6H);3.93(3H);7.05(4H); 7.35(1H);8.2(1H);8.55(1H) |
| 19 | 2-methyl pyridine | OCH2CH2CH2 | 2.02(2H);2.6(6H);3.22(4H); 4.36(2H);6.75(1H);6.85(1H); 7.05(3H);7.35(1H);7.55(1H); 8.15(1H) |
| 20 | 6-amino-1-methyl-2-pyridone | CH2CH2CH2 | 2.1(2H);2.38(2H);2.65(4H); 3.25(4H);4.1(2H);5.4(1H); 5.83(2H);5.9(1H);7.1(4H); 7.35(1H) |
| 21 | 1,6-dimethyl-2-pyridone | CH2CH2CH2 | 1.95(2H);2.4(3H);2.5(2H); 2.6(4H);3.42(4H);4.1(2H); 8.0(1H);6.42(1H);7.05(3H); 7.1(1H);7.35(1H) |
| 22 | 1-methyl-2-pyridone | CH2CH2CH2 | 2.0(2H);2.45(2H);2.6(4H); 3.25(4H);4.02(2H);6.15(1H); 6.57(1H);7.1(3H);7.35(3H) |
| 23 | 5-chloro-1-methyl-2-pyridone | CH2CH2CH2 | 2.0(2H);2.4(2H);2.6(4H); 3.25(4H);4.02(2H);6.55(1H); 7.1 (3H);7.3(2H);7.48(1H) |
| 24 | 3-chloro-2-methyl thiophene | CONHCH2CH2 | 197–200° C. (Hydrochloride) |
| 25 | 2-acetamido-5-methyl pyridine | CONHCH2CH2 | 208–209° C. |
| 26 | 2-methyl pyridine | CH2CONHCH2CH2 | 2.52(2H);2.60(4H);3.25(6H); 3.62(2H);6.65(4H); 7.0–7.45(6H);7.75(1H); 8.18(1H);8.44(1H) Fumarate |
| 27 | 3-methyl thiophene | CH2CONHCH2CH2 | 180–183° C. |
| 28 | 2,5-dimethyl thiophene | CONHCH2CH2 | 2.5(3H);2.7(6H);3.3(4H); 3.55(2H);6.55(1H);6.7(1H); 7.1(3H);7.35(2H) |

-continued

| Example No. | Het | A | Physical data H-NMR [δ, ppm],- Melting Point |
|---|---|---|---|
| 29 | 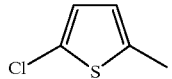 | CONHCH₂CH₂ | 2.68(6H);3.25(4H);3.55(2H); 6.6(1H);6.9(1H);7.1(3H); 7.25(1H);7.35(1H) |
| 30 | 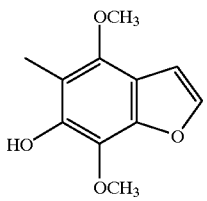 | CONHCH₂CH₂CH₂ | 1.86(2H);2.5(2H);2.65(4H); 6.5(1H);7.05(3H);7.3(1H); 7.75(1H);8.01(1H) |
| 31 | 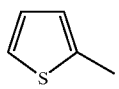 | CH=CHCONHCH₂CH₂ trans | 230° C. Dihydrochloride |
| 32 | 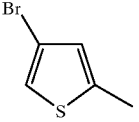 | CH=CHCONHCH₂CH₂ trans | 238–241° C. Dihydrochloride |
| 33 | 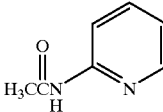 | CONHCH₂CH₂CH₂ | 198–200° C. Fumarate |
| 34 | 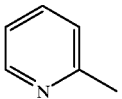 | CONHCH₂CH₂CH₂ | 218–220° C. Dihydrochloride |
| 35 | 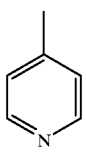 | CONHCH₂CH₂CH₂ | 182–184° C. Dihydrochloride |
| 36 | 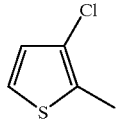 | CONHCH₂CH₂CH₂ | 181–182° C. Dihydrochloride |
| 37 | 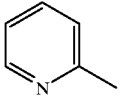 | CH₂CONHCH₂CH₂ | 2.45(2H);2.6(4H);3.25(6H); 3.62(2H);6.6(4H); 7.0–7.42(6H);7.75(1H); 8.18(1H);8.85(1H) Fumarate |
| 38 | 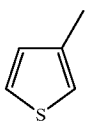 | CH₂CONHCH₂CH₂ | 180–183° C. Dihydrochloride |

-continued

| Example No. | Het | A | Physical data H-NMR [δ, ppm].-Melting Point |
|---|---|---|---|
| 39 | 2,6-dichloro-4-methylpyridine | CONHCH$_2$CH$_2$ | 200–201° C. Dihydrochloride |
| 40 | 4-methylpyridine | CONHCH$_2$CH$_2$ | 178–180° C. Dihydrochloride |
| 41 | 2-methylthiophene | CH$_2$CONHCH$_2$CH$_2$ | 148–150° C. Dihydrochloride |
| 42 | 3-methylpyridine | CONHCH$_2$CH$_2$CH$_2$ | 194–195° C. Dihydrochloride |
| 43 | 2,6-dichloro-4-methylpyridine | CONHCH$_2$CH$_2$CH$_2$ | 201–202° C. Dihydrochloride |
| 44 | 2-methylthiophene | CONHCH$_2$CH$_2$CH$_2$ | 179–181° C. Dihydrochloride |
| 45 | 2,5-dimethylthiophene | CONHCH$_2$CH$_2$CH$_2$ | 153–155° C. Dihydrochloride |
| 46 | 2,3-dimethylthiophene | CONHCH$_2$CH$_2$CH$_2$ | 164–166° C. Dihydrochloride |
| 47 | 2-chloro-5-methylthiophene | CONHCH$_2$CH$_2$CH$_2$ | 138–139° C. Dihydrochloride |
| 48 | 3-chloro-2-methylthiophene | CONHCH$_2$CH$_2$ | 197–200° C. Dihydrochloride |
| 49 | 2-acetamido-5-methylpyridine | CONHCH$_2$CH$_2$ | 208–210° C. Dihydrochloride |

-continued

| Example No. | Het | A | Physical data H-NMR [δ, ppm]- Melting Point |
|---|---|---|---|
| 50 |  | S(CH$_2$)$_3$ | 1.9(2H);2.6(BH);3.1(2H); 3.38(4H);6.22(1H); 6.35(1H);7.07(3H);7.3(2H) |

Examples of pharmaceutical forms:
A) Tablets
Tablets of the following composition are compressed in a tabletting machine in a conventional manner:
- 40 mg of substance from Example 1
- 120 mg of corn starch
- 13.5 mg of gelatin
- 45 mg of lactose
- 2.25 mg of Aerosil® (chemically pure silica in submicroscopically fine dispersion)
- 6.75 mg of potato starch (as 6% strength paste)

B) Sugar-coated tablets
- 20 mg of substance from Example 4
- 60 mg of core composition
- 70 mg of sugar-coating composition The core composition comprises 9 parts of corn starch, 3 parts of lactose and 1 part of vinylpyrrolidone/vinyl acetate 60:40 copolymer. The sugar-coating composition comprises 5 parts of sucrose, 2 parts of corn starch, 2 parts of calcium carbonate and 1 part of talc. The sugar-coated tablets produced in this way are subsequently provided with an enteric coating.

Biological investigations
Receptor-binding studies
Cloned human D$_3$ receptor-expressing CCL 1.3 mouse fibroblasts obtained from Res. Biochemicals Internat. One Strathmore Rd., Natick, Mass. 01760-2148 USA, were used for binding studies.

Cell Preparation
The D$_3$-expressing cells were grown in RPMI-1640 containing 10% fetal calf serum (GIBCO No. 041-32400 N); 100 U/ml penicillin and 0.2% streptomycin (GIBCO BRL, Gaithersburg, Md., USA). After 48 h, the cells were washed with PBS and incubated with 0.05% trypsin-containing PBS for 5 min. Neutralization with medium was then carried out, and the cells were collected by centrifugation at 300×g. To lyze the cells, the pellet was briefly washed with lysis buffer (5 mM tris-HCl, pH 7.4, with 10% glycerol) and then incubated in a concentration of 10$^7$ cells/ml of lysis buffer at 4° C. for 30 min. The cells were centrifuged at 200×g for 10 min and the pellet was stored in liquid nitrogen.

Binding assays
For the D$_3$ receptor-binding assay, the membranes were suspended in incubation buffer (50 mM tris-HCl, pH 7.4, with 120 mM NaCl, 5 mM KCl, 2 mM CaCl$_2$, 2 mM MgCl$_2$, 10 μM quinolinol, 0.1% ascorbic acid and 0.1% BSA) in a concentration of about 10$^6$ cells/250 μl of assay mixture and incubated at 30° C. with 0.1 nM $^{125}$iodosulpiride in the presence and absence of test substance. The non-specific binding was determined using 10$^{-6}$M spiperone.

After 60 min, the free and the bound radioligand was separated by filtration through GF/B glass fiber filters (Whatman, England) on a Skatron cell collector (Skatron, Lier, Norway), and the filters were washed with ice-cold tris-HCl buffer, pH 7.4. The radioactivity collected on the filters was quantified using a Packard 2200 CA liquid scintillation counter.

The K$_i$ values were determined by non-linear regression analysis using the LIGAND program. In this assay, the compounds according to the invention show very high affinities for the D$_3$ receptor and good selectivities with respect to the D$_2$ receptor.

What is claimed is:

1. A composition for treating disorders which respond to dopamine D$_3$ receptor antagonists or agonists which comprises a pharmaceutical aid and an effective amount of a compound of the formula I:

Het—A—B—Ar where

A is a straigh chain or branched C$_3$–C$_8$-alkylene group which contains at least one group which is selected from among O, S, NR$^4$, CONR$^4$, NR$^4$CO, COO, and OCO, B is a radical of the formula:

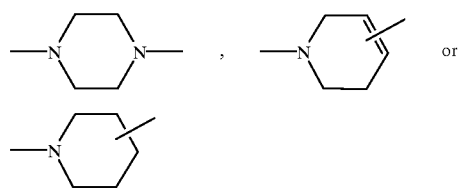

Ar is a phenyl, pyridyl, pyrimidyl or triazinyl, where Ar may have one to four substituents selected from the group consisting of OR$^4$, C$_1$–C$_8$-alkyl, C$_2$–C$_8$-alkenyl, C$_2$–C$_8$-alkynyl, halogen, CN, CO$_2$R$^4$, NO$_2$, SO$_2$R$^4$, SO$_3$R$^4$, NR$^4$R$^5$, SO$_2$NR$^4$R$^5$, SR$^4$, CF$_3$, CHF$_2$, a 5- or a 6-membered carbocyclic, aromatic or non-aromatic ring and a 5- or a 6-membered heterocyclic, aromatic or non-aromatic ring having 1 to 3 hetero atoms which are selected from O, S and N, where the carbocyclic or the heterocyclic ring is unsubsfituted or substituted by C$_1$–C$_8$-alkyl, halogen, OC$_1$–C$_8$-alkyl, OH, NO$_2$ or CF$_3$, and where Ar may also be fused to a 5- or 6-membered carbocyclic, aromatic ring or to a 5- or 6-membered heterocyclic, aromatic or non-aromatic ring having 1 to 3 heteroatoms which are selected from O, S and N, where the carbocyclic or the heterocyclic ring is unsubstituted or substituted by C$_1$–C$_8$-alkyl, halogen, OC$_1$–C$_8$-alkyl, OH, NO$_2$ or CF$_3$, Het is a group

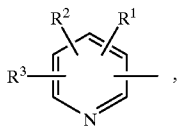

where

R¹, R² and R³ are, independently of one another, H, halogen, $OR^5$, $NR^4R^5$, $SR^4$, $CF_3$, CN or $C_1$–$C_8$-alkyl which is unsubstituted or substituted by OH, $OC_1$-$C_8$-alkyl or halogen, $R^4$ is H or $C_1$–$C_8$-alkyl which is unsubstituted or substituted by OH, $OC_1$-$C_8$-alkyl or halogen, $R^5$ is the meaning indicated for $R^4$ or is $COR^4$ or $CO_2R^4$;

and the salts thereof with physiologically tolerated acids.

2. The composition of claim 1 where

A is a $C_3$–$C_8$-alkylene group which contains O, S or $CONR^4$, and

Ar is a phenyl or pyridyl which may have one or two substituents selected from the group consisting of H, $C_1$–$C_8$-alkyl, $OC_1$–$C_8$-alkyl, $CHF_2$, $CF_3$, CN, halogen, $SO_2OR^4$ and $CO_2R^4$.

3. The composition of claim 5 where

A is a $C_3$–$C_6$-alkylene group which contains S, O or $CONR^4$, and

Ar may carry one or two substituents selected from the group consisting of H, $CF_3$, halogen, $C_1$–$C_8$-alkyl, $OC_1$–$C_8$-alkyl and CN, and B is 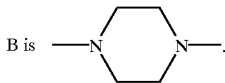.

4. The composition of claim 6 where

R¹, R² and R³ are H, $NR^4R^5$, $OR^5$, $C_1$–$C_8$-alkyl, $CF_3$ or halogen, $R^4$ is H or $C_1$–$C_8$-alkyl, and $R^5$ is H, $C_1$–$C_8$-alkyl or $OC_1$–$C_8$-alkyl.

5. The composition of claim 1 where

A is a $C_3$–$C_6$-alkylene group which contains S, O or CONH,

B is 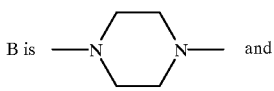 and

B is 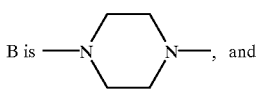, and

Ar may carry one to four substituents selected from the group consisting of H, $CHF_2$, $C_1$–$C_4$-alkyl and $CF_3$.

6. The composition of claim 1 where

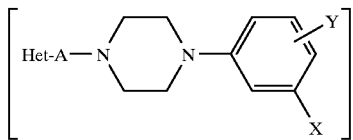

B is 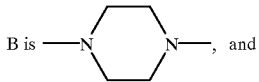, and

Ar is 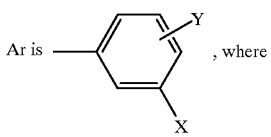, where

X and Y are as defined for the substituents of the radical Ar.

7. The composition of claim 9 where

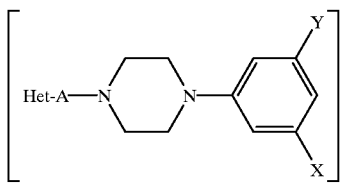

Ar is 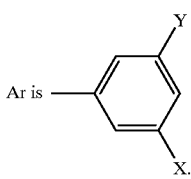.

8. The composition of claim 9, where

Y is H or $C_1$–$C_4$-alkyl, and

X is $CF_3$, $CHF_2$, CN or $C_1$–$C_4$-alkyl.

9. A method of treating disorders which respond to dopamine $D_3$ receptor antagonists or agonists, in which a therapeutically effective amount of a compound as defined in claim 1 is administered to a person requiring such a treatment.

10. The composition of claim 1 wherein Het is

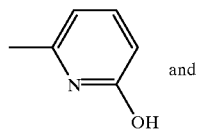 and

A is $S(CH_2)_3$.

* * * * *

UNITED STATES PATENT AND TRADEMARK OFFICE
CERTIFICATE OF CORRECTION

PATENT NO. : 6,090,807
DATED : July 18, 2000
INVENTOR(S) : HELLENDAHL et al.

Page 1 of 2

It is certified that error appears in the above-indentified patent and that said Letters Patent is hereby corrected as shown below:

On the title page, item [57]

In the abstract, line 1, "relate" should be --relates--.
Col. 2, line 12, "NR$^4$ R$^5$" should be --NR$^4$R$^5$--.
Col. 2, line 12, "SO$_2$NR$^5$R$^{5}$" should be --SO$_2$NR$^4$R$^5$--.
Col. 2, line 53, "OC$_1$-C$_3$-alkyl" should be --OC$_1$-C$_8$-alkyl--.
Col. 2, line 55, "and the salts thereof with..." should be on a new line.
Col. 4, line 25, "Bet" should be --Het--.
Col. 5, line 4, "CF$_3$ . CHF$_2$" should be --CF$_3$, CHF$_2$--.
Col. 7, line 33, "carbonyldiizidazole" should be --carbonyldiimidazole--.
Col. 7, line 39, CH$_{2Cl2}$/" should be --CH$_2$Cl$_2$/--.
Col. 8, lines 1-9, delete the formula shown and replace it with:

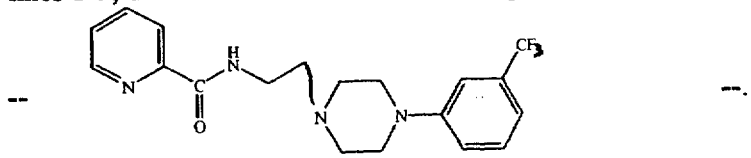

Col. 9/10, NMR-data of compound 10, "7.08(SH)" should be --7.08(5H)--.
Col. 9/10, NMR-data of compound 11, "2.55(2H)" should be --2.56(2H)--.
Col. 9/10, NMR-data of compound 15, "7.35(IH)" should be --7.35(1H)--.
Col. 11/12, NMR-data of compound 21, "8.0(1H)" should be --6.0(1H)--.
Col. 13/14, NMR-data of compound 30, insert --3.25(4H); 3.5(2H); 3.95(6H);--.
Col. 20, claim 7, line 26, "claim 9" should be --claim 6--.

UNITED STATES PATENT AND TRADEMARK OFFICE
CERTIFICATE OF CORRECTION

PATENT NO. : 6,090,807
DATED : July 18, 2000
INVENTOR(S) : HELLENDAHL et al.

It is certified that error appears in the above-indentified patent and that said Letters Patent is hereby corrected as shown below:

Col. 18, claim 1, line 34, "straigh" should be --straight--.

Col. 18, claim 1, line 58, "unsubsfituted" should be --unsubstituted--.

Col. 19, claim 1, line 17, "is the meaning" should be --has the meaning--.

Col. 19, claim 3, line 38, "claim 5" should be --claim 2--.

Col. 19, claim 4, line 41, "claim 6" should be --claim 3--.

Col. 19, claim 5, line 60, delete the line beginning "B is", which is a duplicate.

Col. 20, claim 6, line 2, delete the formula which is bracketed.

Col. 20, claim 6, lines 10-20, after the formulas, delete "." and substitute --,--.

Col. 20, claim 7, line 30, delete the formula which is bracketed.

Col. 20, claim 8, line 45, delete "claim 9" and substitute --claim 6--.

Signed and Sealed this

Twenty-seventh Day of March, 2001

Attest:

Attesting Officer

NICHOLAS P. GODICI

*Acting Director of the United States Patent and Trademark Office*